United States Patent
Gam

(10) Patent No.: US 6,207,731 B1
(45) Date of Patent: Mar. 27, 2001

(54) CATHODE ELECTROCOATING COMPOSITIONS HAVING IMPROVED APPEARANCE, IMPROVED EDGE COVERAGE AND REDUCED CRATERS

(75) Inventor: Allisa Gam, Troy, MI (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/401,697

(22) Filed: Sep. 23, 1999

(51) Int. Cl.$^7$ .................................. C08K 3/20; C08L 63/02
(52) U.S. Cl. .................. 523/404; 204/489; 204/505; 523/414; 523/428; 523/433; 523/435; 556/413; 556/445; 556/463
(58) Field of Search .................................. 523/404, 414, 523/428, 433, 435; 556/413, 445, 463; 204/489, 501, 502, 504, 505, 506

(56) References Cited

U.S. PATENT DOCUMENTS 4,689,131 * 8/1987 Roue et al. ........................... 528/105
5,356,960 10/1994 Chung et al. ........................ 523/404
5,723,519 3/1998 Gam et al. ........................... 523/404

* cited by examiner

Primary Examiner—Robert Dawson
Assistant Examiner—D. Aylward
(74) Attorney, Agent, or Firm—Joseph A. Tessari

(57) ABSTRACT

A cathodic electrocoating composition comprises an aqueous carrier, a film forming binder, comprising an epoxy-amine adduct and a blocked polyisocyanate crosslinking agent, dispersed in the carrier, and a novel additive comprising the reaction product of (1) a polyoxy alkylene di or monoamine; (2) a glycidoxy alkyl alkoxy silane; and (3) a glycidyl compound selected from the group consisting of a glycidyl ester of a carboxylic acid and an alkyl glycidyl ether, which reaction product is hydrolyzed in the presence of acid and water to convert alkoxysilane moieties to silanol moieties. The electrocoat composition produces coatings having a smoother appearance with better edge coverage and fewer craters.

14 Claims, No Drawings

CATHODE ELECTROCOATING COMPOSITIONS HAVING IMPROVED APPEARANCE, IMPROVED EDGE COVERAGE AND REDUCED CRATERS

BACKGROUND OF THE INVENTION

This invention is directed to a cathodic electrocoating composition and in particular to a cathodic electrocoating composition containing an anticrater agent which significantly reduces craters and improves edge coverage of an electrodeposited film of the composition.

The coating of electrically conductive substrates by an electrodeposition process, also called an electrocoating process, is a well known and important industrial process. Electrodeposition of primers to automotive substrates is widely used in the automotive industry. In this process, a conductive article, such as an auto body or an auto part, is immersed in a bath of a coating composition of an aqueous emulsion of film forming polymer and acts as an electrode in the electrodeposition process. An electric current is passed between the article and a counter-electrode in electrical contact with the aqueous emulsion, until a desired coating is deposited on the article. In a cathodic electrocoating process, the article to be coated is the cathode and the counter-electrode is the anode.

Resin compositions used in the bath of a typical cathodic electrodeposition process also are well known in the art. These resins typically are made from polyepoxide resins which have been chain extended and then an adduct is formed to include amine groups in the resin. Amine groups typically are introduced through reaction of the resin with an amine compound. These resins are blended with a crosslinking agent and then neutralized with an acid to form a water emulsion which is usually referred to as a principal emulsion. Pigment paste, coalescent solvents, water, and other additives are combined with the principal emulsion to form the electrocoating bath.

The electrocoating bath is placed in an insulated tank containing the anode. The article to be coated is the cathode and is passed through the tank containing the electrodeposition bath. The thickness of the coating that is deposited on the article being electrocoated is a function of the bath characteristics, the electrical operating characteristics of the tank, the immersion time, and the like. The resulting coated article is removed from the bath after a set period of time and is rinsed with deionized water. The coating on the article is cured typically in an oven at sufficient temperature to produce a crosslinked finish on the article.

Continuing problems with cathodic electrocoating compositions have been the lack of smoothness in the cured finish, the presence of craters in the cured finish, and the lack of edge protection or edge coverage of the composition. There have been various additives proposed in the art to address one or more of these problems. U.S. Pat. No. 5,356,960, for example, discloses an anticrater additive. However, this additive has a tendency to migrate to the surface of the electrocoating after baking, resulting in poor adhesion of primers or other coatings used in the automotive and other industries. U.S. Pat. No. 5,723,519 discloses an anticrater agent which does not migrate during baking and thus overcomes the disadvantages noted above and additionally is said to improves edge coverage. However, there is still a need for electrocoat compositions that have improved appearance, a lack of craters, and improved coverage at the edges of the coated substrate.

SUMMARY OF THE INVENTION

An improved aqueous cathodic electrocoating composition having a binder of an epoxy-amine adduct and a blocked polyisocyanate crosslinking agent; and a novel additive that provides improved appearance, improved edge coverage and reduces the incidence of craters in a substrate coated with the composition. The novel additive is the reaction product of polyoxyalkylene amine (either a diamine or a monoamine); a glycidoxy alkyl alkoxysilane and a glycidyl compound selected from the group consisting of glycidyl esters of carboxylic acids and alkyl glycidyl ethers. The additive is then emulsified in water with acid to hydrolyze the alkoxysilane moieties to silanol moieties.

DETAILED DESCRIPTION OF THE INVENTION

The novel additive forming the basis of this invention is readily incorporated into the electrocoating composition by emulsifying it in water with organic or inorganic acid and then adding it to an aqueous electrocoating composition. The additive remains stable in the composition and in the electrocoating bath for extended periods of time under conventional bath operating conditions since it is not reactive with the other constituents in the composition, it does not adversely affect other properties of the electrocoating bath or finishes of the electrocoating composition; and provides cured finishes that are smoother than the prior art with improved edge protection and less crater formation.

The additive is prepared by reacting a polyoxyalkylene amine (diamine or monoamine) with glycidoxy alkyl alkoxy silane and either a glycidyl ester of a carboxylic acid or an alkyl glycidyl ether. The mole ratios of polyoxyalkylene amine to glycidoxy alkyl alkoxysilane to glycidyl ester or ether is in the range of 1:0.2:1.8 to 1:1.2:0.8. Generally, the reaction is carried out at a temperature of 50° C. to 130° C. until there is no residual epoxy present (about 1 to 6 hours). The additive is then emulsified in water with organic or inorganic acid, which hydrolyzes the alkoxysilane groups to stable silanol moieties. Examples of suitable organic acids include lactic acid, acetic acid and formic acid. Inorganic acids, such as, for example, sulfamic acid and alkane sulfonic acids such as methane sulfonic acid, or phosphoric acid may also be used.

The polyoxyalkylene di- or monoamine used to form the novel additive has 2–4 carbon atoms in the alkylene group and preferably is polyoxypropylene di- or monoamine having number average molecular weight of about 230 to 3,000 preferably, 1,500 to 2,500, such as Jeffamine®D-2000 having a number average molecular weight of about 2000 available from Huntsman Corporation. Other useful polyoxyalkylene amines include polyoxyethylene di- or monoamines and polyoxybutylene di- or monoamines of similar molecular weight.

Typically useful glycidoxy alkyl alkoxy silanes used to make the novel additive have the formula:

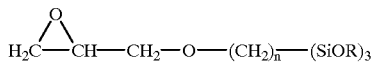

where R is methyl, ethyl, or a mixture of methyl and ethyl and n is 1–3. Typical silanes are gamma-glycidoxy propyl trimethoxy silane, gamma-glycidoxy ethyl trimethoxy silane, gamma-glycidoxy methyl trimethoxy silane, gamma-glycidoxy methyl triethoxy silane, gamma-glycidoxy ethyl triethoxy silane, gamma-glycidoxy propyl triethoxy silane. Gamma-glycidoxy propyl trimethoxy silane is preferred to form a high quality additive.

Typical useful glycidyl esters and ethers include monoglycidyl esters, monoglycidyl ethers, polyglycidyl esters and polyglycidyl ethers. Preferred are the monoglycidyl esters and monoglycidyl ethers. Representative examples of monoglycidyl ethers and esters that may be used to advantage include 2-ethylhexyl glycidyl ether, butyl glycidyl ether, dodecyl glycidyl ether, glycidyl ester of neodecanoic acid and glycidyl ester of pivalic acid. Monoglycidyl ester of neodecanoic acid is particularly preferred and provides coatings with lower gloss and better (smoother) appearance.

The additive is emulsified in water with an organic or inorganic acid (mentioned above) to hydrolyze the silane group to form silanol groups. The additive can then be added to the electrocoating composition at almost any time and can be added to the principal emulsion, or to the bath.

The additive after complete hydrolysis has the following structural formula:

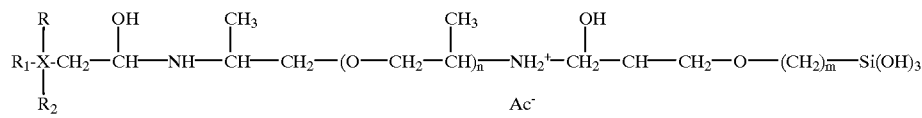

where R, $R_1$ and $R_2$ are independently H or $C_aH_{2a+1}$, where a is an integer of 0–22; n is an integer of 5–40; m is an integer of 1–3; and X is an either or ester linkage.

Generally, the additive is used in the electrocoating composition at a level of at least 2% by weight, based on the total weight of binder solids in the electrocoating composition and, preferably, it is used at a level of about 2% to 10% by weight. More preferably, about 4% to 8% by weight of the additive is used.

Most principal emulsions used in an electrocoating composition comprise an aqueous emulsion of a binder of an epoxy amine adduct blended with a crosslinking agent which has been neutralized with an acid to form a water soluble product. The binder of the electrocoating composition typically is a blend of an epoxy arnine adduct and a blocked polyisocyanate crosslinking agent. While the novel additive is potentially usable with a variety of different cathodic electrocoat resins, the epoxy amine adduct resins are particularly preferred. These resins are generally disclosed in U.S. Pat. No. 4,419,467 which is incorporated by reference.

Preferred crosslinkers for the epoxy amine adduct resins are also well known in the prior art. These are aliphatic, cycloaliphatic and aromatic isocyanates such as hexamethylene diisocyanate, cyclohexamethylene diisocyanate, toluene diisocyanate, methylene diphenyl diisocyanate and the like. These isocyanates are pre-reacted with a blocking agent such as oximes, alcohols, or caprolactams which block the isocyanate functionality, i.e., the crosslinking functionality. Upon heating the blocking agents separate, thereby providing a reactive isocyanate group and crosslinking occurs. Isocyanate crosslinkers and blocking agents are well known in the prior art and also are disclosed in the aforementioned U.S. Pat. No. 4,419,467.

The cathodic binder of the epoxy amine adduct and the blocked isocyanate are the principal resinous ingredients in the electrocoating composition and are usually present in amounts of about 30 to 50% by weight of solids of the composition. To form an electrocoating bath, the solids are generally reduced with an aqueous medium.

Besides the binder resin described above, the electrocoating composition usually contains pigment which is incorporated into the composition in the form of a pigment paste. The pigment paste is prepared by grinding or dispersing a pigment into a grinding vehicle and optional ingredients such as wetting agents, surfactants, and defoamers. Any of the pigment grinding vehicles that are well known in the art can be used or the novel additive described above can be used. After grinding, the particle size of the pigment should be as small as practical, generally, the particle size is about 6–8 using a Hegman grinding gauge.

Pigments which can be used in this invention include titanium dioxide, basic lead silicate, strontium chromate, carbon black, iron oxide, clay and the like. Pigments with high surface areas and oil absorbencies should be used judiciously because these can have an undesirable affect on coalescence and flow of the electrodeposited coating.

The pigment to binder weight ratio is also important and should be preferably less than 0.5:1, more preferably less than 0.4:1, and usually about 0.2:1 to 0.4:1. Higher pigment to binder weight ratios have been found to adversely affect coalescence and flow.

The coating compositions of the invention can contain optional ingredients such as wetting agents, surfactants, defoamers and the like. Examples of surfactants and wetting agents include alkyl imidazolines such as those available from Ciba-Geigy Industrial Chemicals as "Amine C", acetylenic alcohols available from Air Products and Chemicals as "Surfynol®104". These optional ingredients, when present, constitute from about 0.1 to 20 percent by weight of binder solids of the composition.

Optionally, plasticizers can be used to promote flow. Examples of useful plasticizers are high boiling water immiscible materials such as ethylene or propylene oxide adducts of nonyl phenols or bisphenol A. Plasticizers are usually used at levels of about 0.1 to 15 percent by weight resin solids.

The electrocoating composition of this invention is an aqueous dispersion. The term "dispersion" as used within the context of this invention is believed to be a two-phase translucent or opaque aqueous resinous binder system in which the binder is in the dispersed phase and water the continuous phase. The average particle size diameter of the binder phase is about 0.1 to 10 microns, preferably, less than 5 microns. The concentrations of the binder in the aqueous medium in general is not critical, but ordinarily the major portion of the aqueous dispersion is water. The aqueous dispersion usually contains from about 3 to 50 percent preferably 5 to 40 percent by weight binder solids. Aqueous binder concentrates which are to be further diluted with water when added to an electrocoating bath, generally have a range of binder solids of 10 to 30 percent weight.

The following example illustrates the invention. All parts and percentages are on a weight basis unless otherwise indicated.

EXAMPLE
Preparation of Anticrater Agent

The anticrater agent was prepared by charging 1000 parts of Jeffamine D2000® (polyoxypropylene diamine having a number molecular weight of 2000 and an amine equivalent of 996.5), 100 parts of Cardura®E-10 (glycidyl ester of neodecanoic acid), 141.6 parts of Silquest®A-187 (glycidoxy propyl trimethoxysilane) and 130 parts of 2-ethyl hexanol into a suitable reaction vessel and heated to 110° C. under a dry nitrogen blanket. The reaction mixture was maintained at 110° C. until a Gardner-Holdt viscosity of S-T was obtained. The adduct was then dispersed in an aqueous medium of 4049.6 parts of deionized water and 66.3 parts of lactic acid. The resulting adduct solution had a nonvolatile content of 22%.

Preparation of Crosslinking Resin Solution

An alcohol blocked polyisocyanate crosslinking resin solution was prepared by charging 317.14 parts of Mondur® MR (methylene diphenyl diisocyanate), 47.98 parts of methyl isobutyl ketone and 0.064 parts of dibutyl tin dilaurate into a suitable reaction vessel and heated to 37° C. under a nitrogen blanket. A mixture of 323.10 parts of diethylene glycol mono butyl ether and 13.04 parts of trimethylolpropane was slowly charged into the reaction vessel while maintaining the reaction mixture below 93° C. The reaction mixture was then held at 110° C. until essentially all of the isocyanate was reacted as indicated by infrared scan of the reaction mixture. 2.30 parts of butanol and 167.37 parts of methyl isobutyl ketone were then added. The resulting resin solution had a nonvolatile content of 75%.

Preparation of Chain Extended Polyepoxide Emulsion

The following ingredients were charged into a suitable reaction vessel: 1478 parts of Epon 828® (Epoxy resin of diglycidyl ether of bisphenol A having an epoxy equivalent weight of 188); 427 parts bisphenol A; 533 parts ethoxylated bisphenol A having a hydroxy equivalent weight of 247 (Synfac®8009) and 121 parts xylene. The resulting reaction mixture was heated to 160° C. under nitrogen blanket and held at room temperature for 1 hour. 5.1 parts dimethyl benzyl amine were added and the mixture was held at 182° C. until an epoxy equivalent weight of 1050 was obtained. When the reaction mixture cooled to 149° C., then 2061 parts of crosslinker resin solution (from above) was added. When the reaction temperature cooled to 107° C., 168 parts of diketimine (reaction product of diethylenetriamine and methyl isobutyl ketone having a nonvolatile content of 72.27%) and 143 parts of methyl ethanol amine were added. The temperature of the resulting mixture rose and was held at 120° C. for 1 hour and then dispersed in an aqueous medium of 3886 parts deionized water and 182.6 parts lactic acid (88% lactic acid in deionized water). An additional 2741 parts of deionized water was added. The emulsion was kept agitated until the methyl isobutyl ketone was evaporated. The resulting resin emulsion had a nonvolatile content of 38%.

Preparation of Quaternizing Agent

The quaternizing agent was prepared by adding 87 parts dimethylethanolamine to 320 parts ethylhexanol half-capped toluene diisocyanate in the reaction vessel at room temperature. An exothermic reaction occurred and the reaction mixture was stirred for one hour at 80° C. 118 parts aqueous lactic acid solution (75% nonvolatile content) was then added followed by the addition of 39 parts 2-butoxyethanol. The reaction mixture was held for about one hour at 65° C. with constant stirring to form the quaternizing agent.

Preparation of Pigment Grinding Vehicle

The pigment grinding vehicle was prepared by charging 710 parts Epon®828 (diglycidyl ether of bisphenol A having an epoxide equivalent weight of 188) and 290 parts bisphenol A into a suitable vessel under nitrogen blanket and heated to 150° C.–160° C. to initiate an exothermic reaction. The exothermic reaction was continued for about one hour at 150° C.–160° C. The reaction mixture was then cooled to 120° C. and 496 part of 2-ethylhexanol half capped toluene diisocyanate was added. The temperature of the reaction mixture was held at 110° C.–120° C. for one hour, followed by the addition of 1095 parts of 2-butoxyethanol, the reaction mixture was then cooled to 85° C.–90° C. and then 71 parts of deionized water was added followed by the addition of 496 parts quarternizing agent (prepared above). The temperature of the reaction mixture was held at 85° C.–90° C. until an acid value of about 1 was obtained.

| Preparation of Pigment Paste | |
|---|---|
| Ingredient | Parts by Weight |
| Pigment grinding vehicle (prepared above) | 608.52 |
| Deionized Water | 1244.42 |
| Titanium dioxide pigment | 713.81 |
| Aluminum silicate pigment | 149.12 |
| Lead silicate pigment | 114.71 |
| Carbon black pigment | 19.61 |
| Dibutyl tin oxide | 149.81 |

The above ingredients were mixed in a suitable container until a homogenous mixture was formed. They were then dispersed by charging the mixture into a Eiger mill and then grinding until a Hegman reading of 7 or greater was obtained.

Preparation of Electrocoating Baths

| Ingredient | Parts by Weight | | | |
| --- | --- | --- | --- | --- |
| | Bath I | Bath II | Bath III | Bath IV |
| Emulsion | 1503.08 | 1518.90 | 1503.08 | 1487.26 |
| Deionized Water | 2013.49 | 1974.25 | 1962.74 | 1951.23 |
| Pigment Paste | 397.54 | 397.54 | 397.54 | 397.54 |
| Anticrater Agent | 85.89* | 109.31 | 136.64 | 163.97 |
| Total | 4000.00 | 4000.00 | 4000.00 | 4000.00 |

*The anticrater agent used in Bath I comprised a conventional anticrater agent which is the reaction product of Jeffamine ® D2000 (polyoxyalkylene diamine) and Epon ® 1001 epoxy resin.

Each of the cationic electrocoating baths were prepared by mixing the ingredients together, and then ultrafiltering the mixtures. Each bath was electrocoated at 240 to 280 volts to obtain 0.8–1.0 mils (20.23–25.4 microns). The baths were then compared for crater resistance, surface roughness and edge corrosion resistance. Bath I served as the control.

ASPP blow out crater test is used to test each bath. Crater resistance was rated according to the following rating scale of A–E:

A—0–10% defects
B—11–20% defects
C—21–40% defects
D—41–80% defects
E—Greater than 80% defects The crater resistant rating for Bath I (control) was E. Baths II, III and IV each rated an A on crater resistance.

In order to measure edge corrosion resistance, razor blades were electrocoated in each of Baths I, II, III and IV and baked at 360° C. for 10 minutes metal temperature. The razor blades then were exposed to salt spray for 7 days. The number of rust spots on each blade were counted by viewing the blades under a microscope. The blades from Bath I had 100–140 rust spots, the blades from Bath II had 60–80 rust spots, the blades from Bath III had 20–40 rust spots, and the blades from Bath IV had 0 rust spots.

The surface roughness of the electrocoat cured films was measured by coating phosphated cold steel panels in Baths I, II, III and IV and baked at 360° C. for 10 minutes metal temperature. The resulting film thickness was 0.8 to 0.9 mils. The surface roughness was measured using a Taylor-Hobson Surtronic 3+ profilometer. The surface roughness of the panels from Bath I was 254 nm (10 μinch); with Bath II was 356 nm (14 μinch); with Bath III was 457 nm (18 μinch) and with Bath IV was 559 nm (22 μinch).

What is claimed is:

1. A cathodic electrocoating composition, comprising
   a) an aqueous carrier;
   b) a film forming binder dispersed in the carrier, said binder comprising an epoxy-amine adduct and a blocked polyisocyanate crosslinking agent; and
   c) an additive comprising the reaction product of:
      1) a polyoxy alkylene amine;
      2) a glycidoxy alkyl alkoxy silane; and
      3) a glycidyl compound selected from the group consisting of
         (a) a glycidyl ester of a carboxylic acid and
         (b) an alkyl glycidyl ether;
   which reaction product is hydrolyzed in the presence of acid and water to convert alkoxysilane moieties to silanol moieties.

2. The improved electrocoating composition of claim 1 wherein the glycidyl compound is selected from the group consisting of 2-ethylhexyl glycidyl ether, butyl glycidyl ether, dodecyl glycidyl ether, glycidyl ester of neodecanoic acid and glycidyl ester of pivalic acid.

3. The improved electrocoating composition of claim 2, wherein the glycidyl compound is monoglycidyl ester of neodecanoic acid.

4. The improved electrocoat composition of claim 2, wherein the polyoxyalkylene amine is a polyoxypropylene amine having a weight average molecular weight of about 230–3,000.

5. The improved electrocoating composition of claim 2, wherein the glycidoxy alkyl alkoxy silane is an gamma-glycidoxy propyl trimethoxy silane.

6. The improved electrocoating composition of claim 1, wherein the polyoxyalkylene amine is selected from the group consisting of polyoxyalkylene diamines and polyoxyalkylene monoamines.

7. The improved electrocoating composition of claim 1, wherein the polyoxyalkylene amine is polyoxypropylene diamine having a weight average molecular weight of about 230–3,000; wherein the glycidoxy alkyl alkoxy silane is gamma-glycidoxy propyl trimethoxy silane; and wherein the glycidyl compound is a monoglycidyl ester of a carboxylic acid.

8. The improved electrocoat composition of claim 1, wherein the mole ratio of polyoxyalkylene amine to glycidoxy alkyl silane to glycidyl compound is in the range of 1:0.2:1.8 to 1:1.2:0.8.

9. The improved cathodic electrocoating composition of claim 1 wherein the additive is present in an amount of about 2% to 10% by weight, based on the weight of the film forming binder of the composition.

10. An additive for a cathodic electrocoat composition having the structural formula (after hydrolysis):

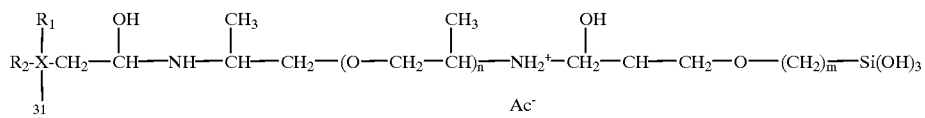

where $R_1$, $R_2$ and $R_3$ are independently H or $C_aH_{2a+1}$ where a is an integer of 0–22; n is an integer of 5–40; m is an integer of 1–3; and X is an either or ester linkage.

11. In a method of preparing a cathodic electrocoating composition comprising the following steps in any workable order:
   (a) preparing an epoxy-amine adduct;

(b) preparing a blocked polyisocyanate crosslinking agent;

(c) blending the epoxy-amine adduct with the blocked polyisocyanate crosslinking agent;

(d) neutralizing the epoxy-amine adduct with an organic acid to form an emulsion;

(e) blending the emulsion with a pigment paste; and (f) incorporating an additive agent to the electrocoating composition; wherein the additive consists essentially of a reaction product of polyoxyalkylene amine, a glycidoxy alkyl alkoxy silane and a glycidyl compound selected from the group consisting of a glycidyl ester of a carboxylic acid and an alkyl glycidyl ether, which reaction product is hydrolyzed to convert alkoxysilane moieties to silanol moieties.

12. The method of claim 11 wherein the glycidyl compound is selected from the group consisting of 2-ethylhexyl glycidyl ether, butyl glycidyl ether, dodecyl glycidyl ether, glycidyl ester of neodecanoic acid and glycidyl ester of pivalic acid.

13. The method of claim 12, wherein the glycidyl compound is monoglycidyl ester of neodecanoic acid.

14. The method of claim 11 wherein the mole ratio of polyoxyalkylene amine to glycidoxy alkyl silane to glycidyl compound is in the range of 1:0.2:1.8 to 1:1.2:0.8.

* * * * *